(12) United States Patent
Dembri

(10) Patent No.: US 11,844,676 B2
(45) Date of Patent: Dec. 19, 2023

(54) PERSONAL HYGIENE PRODUCT

(71) Applicant: Hakim Rabah Dembri, Bradenton, FL (US)

(72) Inventor: Hakim Rabah Dembri, Bradenton, FL (US)

( * ) Notice: Subject to any disclaimer, the term of this patent is extended or adjusted under 35 U.S.C. 154(b) by 1078 days.

(21) Appl. No.: 16/535,706

(22) Filed: Aug. 8, 2019

(65) Prior Publication Data
US 2020/0046575 A1 Feb. 13, 2020

Related U.S. Application Data

(60) Provisional application No. 62/715,923, filed on Aug. 8, 2018.

(51) Int. Cl.
*A61F 13/47* (2006.01)
*A61F 13/84* (2006.01)
*A61F 13/64* (2006.01)
*A61F 13/15* (2006.01)

(52) U.S. Cl.
CPC .............. *A61F 13/47* (2013.01); *A61F 13/64* (2013.01); *A61F 13/8405* (2013.01); *A61F 2013/1513* (2013.01); *A61F 2013/8408* (2013.01)

(58) Field of Classification Search
None
See application file for complete search history.

(56) References Cited

U.S. PATENT DOCUMENTS

| | | | | | |
|---|---|---|---|---|---|
| 235,884 | A * | 12/1880 | Korff | | A61F 13/20 604/358 |
| 2,076,526 | A * | 4/1937 | Brown | | A61F 13/2008 604/375 |
| 2,134,930 | A * | 11/1938 | Reynolds | | A61F 13/2085 604/377 |
| 2,831,485 | A * | 4/1958 | Haeseler | | A61F 13/2051 604/385.18 |
| 4,200,101 | A * | 4/1980 | Glassman | | A61F 13/2051 604/385.18 |
| 8,926,581 | B1 * | 1/2015 | Acosta | | A41D 27/12 604/401 |
| 9,603,749 | B2 * | 3/2017 | Hart | | A61F 13/126 |
| 2001/0056268 | A1 * | 12/2001 | Mizutani | | A61F 13/4753 604/385.27 |
| 2005/0187502 | A1 * | 8/2005 | Krempel | | A61F 7/103 602/5 |
| 2010/0130907 | A1 * | 5/2010 | Linkel | | A61F 13/206 156/196 |
| 2014/0188064 | A1 * | 7/2014 | Yamaki | | A61F 13/206 604/385.18 |
| 2015/0366727 | A1 * | 12/2015 | Lepke | | A61F 13/12 604/377 |
| 2016/0296383 | A1 * | 10/2016 | Atkins | | A61F 13/42 |

FOREIGN PATENT DOCUMENTS

KR 20080079759 A * 2/2008

* cited by examiner

*Primary Examiner* — Bradley H Philips
(74) *Attorney, Agent, or Firm* — von Briesen & Roper, s.c.

(57) ABSTRACT

A personal hygiene product for maintaining dryness in the intergluteal cleft is provided. The personal hygiene product may include an absorbent substrate having a proximal end and a distal end, and a tether extending through the absorbent substrate, the tether having a first end and a second end, the first end extending past the absorbent substrate proximal end, the second end extending past the absorbent substrate distal end.

6 Claims, 2 Drawing Sheets

PERSONAL HYGIENE PRODUCT

CROSS-REFERENCE TO RELATED APPLICATION

This application is a non-provisional patent application claiming priority under 35 USC § 119(e) to U.S. Provisional Patent Application Ser. No. 62/715,923 filed on Aug. 8, 2018.

TECHNICAL FIELD

The present disclosure relates generally to personal hygiene products and, more specifically, relates to personal hygiene products for keeping the intergluteal cleft dry.

BACKGROUND

Human beings perspire. It is the body's natural response for lowering its temperature for proper functioning. While effective, it of course has certain drawbacks. Sweating under the arms is unsightly and can cause perspiration to soak through the shirt or other garment being worn. Sweating on the upper lip or face can also be unsightly and cause unease through self-consciousness. Sweating of the hands can be socially embarrassing. Sweating of the feet can cause odor and discomfort and as well as potentially conditions such as athlete's foot and toenail fungus. Sweating around the groin cause chaffing, odor and discomfort.

Over time, systems and products have been developed to alleviate such situations. For example, deodorants have been used under the arms for decades and mask the odor caused by such perspiration. Anti-perspirants have also been used for many years. Rather than just mask the odor, antiperspirants attempt to prevent release of the perspiration at all by blocking the sweat glands of the armpit. Facial sweating is often combatted with cosmetics such as powders or creams. Sweating of the feet can be alleviated by proper footwear and inserts.

However, one area of personal hygiene and sweat absorption that still needs to be addressed is with regard to sweating around the groin, specifically within the intergluteal cleft. The intergluteal cleft, also known as the butt crack, is a groove-like region between the gluteus muscles running from the sacrum to the perineum. While essential for walking, running and other movements, the structure and location of the intergluteal cleft invited significant sweat to be generated. This condition can be exacerbated by such things as exercise, climate, obesity and diet. Moreover, as the intergluteal cleft terminates at the perineum, which is proximate the anus, anal discharge can also be communicated to the intergluteal cleft causing more discomfort or odor.

From the foregoing, it can be seen that a need exists for improvements in the ability to keep the intergluteal cleft dry.

SUMMARY

In accordance with an aspect of the present disclosure, an intergluteal cleft personal hygiene product is disclosed. The intergluteal cleft personal hygiene product may include an absorbent substrate having a proximal end and a distal end, and a tether extending through the absorbent substrate, the tether having a first end and a second end, the first end extending past the absorbent substrate proximal end, the second end extending past the absorbent substrate distal end.

In accordance with another aspect of the present disclosure, an intergluteal cleft personal hygiene product is disclosed. The intergluteal cleft personal hygiene product may include an absorbent substrate, the absorbent substrate being elongated with proximal and distal ends, the elongated absorbent substrate having a length sufficient to extend from a sacrum to a perineum of an adult human.

In accordance with yet another aspect of the present disclosure, a method for maintaining an intergluteal cleft in a dry condition is disclosed. The method may include the steps of providing a personal hygiene product, the personal hygiene product having an absorbent substrate with a proximal end and a distal end, inserting the personal hygiene product into the intergluteal cleft, and absorbing sweat with the personal hygiene product.

These and other aspects and features of the present disclosure will be more readily understood upon reading the following detailed description when taken in conjunction with the accompanying drawings.

Figure 1:
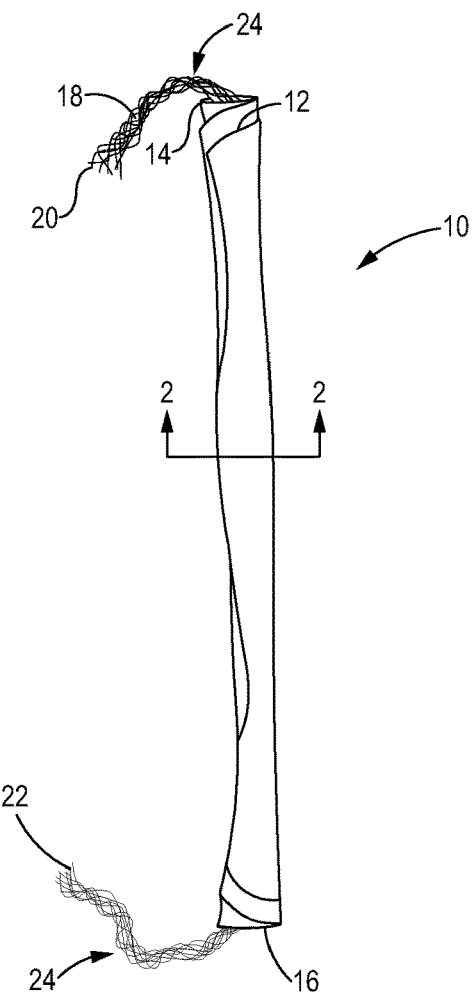
FIG. 1 is a perspective view of an intergluteal cleft personal hygiene product according to one embodiment of the present disclosure.

While the present disclosure is susceptible to various modifications and alternative constructions, certain illustrative embodiments thereof have been shown in the drawings and will be described below in detail. It should be understood, however, that there is no intention to limit the present invention to the specific forms disclosed, but on the contrary, the intention is to cover all modifications, alternative constructions, and equivalents falling with the spirit and scope of the present invention.

DETAILED DESCRIPTION

Referring now to the drawings, and with specific reference to FIG. 1, a personal hygiene product used for a maintaining dryness in the intergluteal cleft is generally referred to by reference numeral 10. As shown therein, the intergluteal cleft personal hygiene product 10 is generally elongate in nature. While not depicted, the intergluteal cleft personal hygiene product 10 is designed to be sufficiently long to extend from the sacrum to the perineum with the intergluteal cleft of an adult human being.

Figure 2:
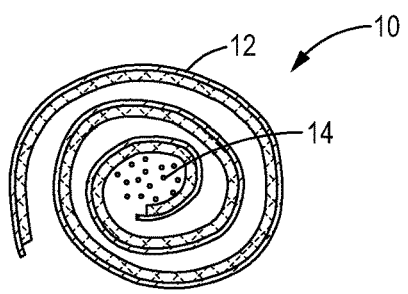
FIG. 2 is a cross-sectional view of the intergluteal cleft personal hygiene product of FIG. 1, taken along line 2-2 of FIG. 1.

With reference again to FIG. 1, the intergluteal cleft personal hygiene product 10 is shown to include an absorbent substrate 12. The absorbent substrate 12 may be manufactured from any suitable absorbent material of fabric such as but not limited to cotton and paper. As shown therein, the absorbent substrate 12 may be a flat sheet rolled or folded over onto itself, or may be a solid core of absorbent material. The resulting absorbent substrate 12 may be provided in the flat configuration of FIG. 1 (also see the cross-sectional view of FIG. 2) or may be provided in any number of other cross-sectional shapes such as round, oval, triangular, polygonal, and the like.

As for dimensions, the present disclosure is not limited to any specific length or width. However, as the intergluteal cleft personal hygiene product 10 is designed for insertion into a human intergluteal cleft, it may be manufactured so as to accommodate a typical range of human sizes. For example, from a proximal end 14 to a distal end 16, the intergluteal cleft personal hygiene product 10 may be two to twenty inches long, but may be shorter or longer. Similarly, it may be a quarter inch to 1 inch wide, but less and greater widths are possible as well.

In addition, to the absorbent substrate 12, it will be noted that in the embodiment of FIG. 1, the intergluteal cleft personal hygiene product 10 may also include a tether 18. While the tether 18 is shown being manufactured from cotton, other materials including but not limited to other fabrics, papers and plastics are possible. From the drawing, it will be appreciated that the tether 18 extends through the entire length of the intergluteal cleft personal hygiene product 10. More specifically, the tether 18 includes a first end 20 that extends past the proximal end 14, and a second end 22 that extends past the distal end 16. In so doing, the tether 18 forms applicator handles 24 to facilitate insertion and removal of the personal hygiene product 10 into an intergluteal cleft of a user.

Figure 3:
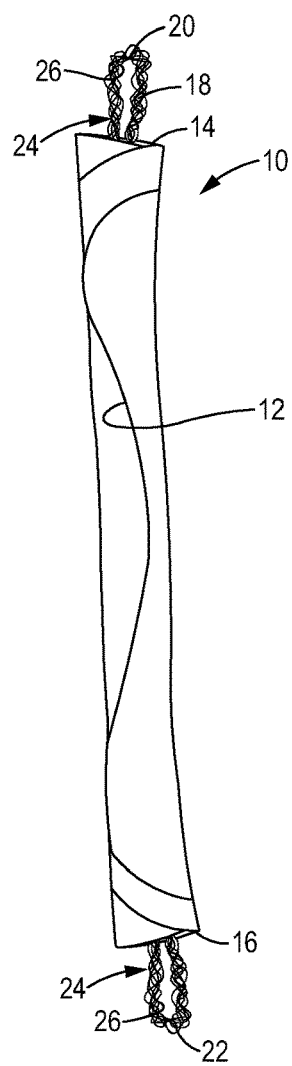
FIG. 3 is a perspective view of an intergluteal cleft personal hygiene product according to another embodiment of the present disclosure.

FIG. 3 depicts a second embodiment of the intergluteal cleft personal hygiene product 10. As shown therein, the intergluteal cleft personal hygiene product 10 of FIG. 3 is the same as that of FIG. 1, but for the provision of loops 26 in the tether 18. The loops 26 are provided to enable a user a more readily graspable applicator handle 24. In addition, the tether 18 of FIG. 3 may be provided as one continuous loop of string or twine. In so doing, the tether may be more robust and durable.

Figure 4:
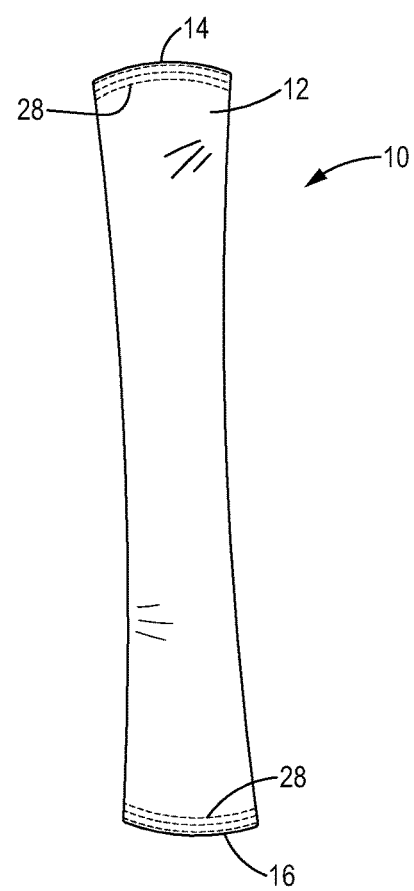
FIG. 4 is a perspective view of an intergluteal cleft personal hygiene product according to another embodiment of the present disclosure.

FIG. 4 depicts another embodiment of the intergluteal cleft personal hygiene product 10. As will be noted, the embodiment of FIG. 4 is provided without a tether 18. Rather, the absorbent substrate 12 of the embodiment of FIG. 4 terminates at proximal and distal ends 14 and 16 with a plurality of stitches 28 holding the folds of the absorbent substrate 12 together.

In operation, the present disclosure provides a sanitary solution to the problems of intergluteal cleft sweating and anal discharge. In a first step, an intergluteal cleft personal hygiene product 10 is provided. In a second step, a human user inserts the intergluteal cleft personal hygiene product 10 into his or her intergluteal cleft. The user will align the intergluteal cleft personal hygiene product 10 so as to extend from the sacrum to the perineum. If the tether 18 is provided, the use may grasp the application handles 24 provided thereby with one in each hand so to most effectively locate same. Moreover, using the natural compressive bias provided by the gluteal muscles, and the malleable soft construction of the intergluteal cleft personal hygiene product 10, the intergluteal cleft personal hygiene product 10 is naturally held in place once inserted.

During use, the intergluteal cleft personal hygiene product 10 absorbs perspiration generated and/or communicated to the intergluteal cleft. Moreover, given its location over or proximate to the anus, the intergluteal cleft personal hygiene product 10 also absorbs any anal discharge generated by the user as well. After a period of time, and/or upon using the bathroom, the user can remove the intergluteal cleft personal hygiene product 10, discard same, and insert a new one. In so doing, the user is kept clean, dry, comfortable and less malodorous.

From the foregoing, it can be seen that the present disclosure provides a personal hygiene product for maintaining the intergluteal cleft in a clean, dry and comfortable state. By providing the intergluteal cleft personal hygiene product in a various of lengths, widths and cross-sectional shapes, the ideal fit for each individual user is also ensured. Moreover, by providing tethers, looped or otherwise, as well as stitched ends, convenient applicator handles are provided so as to enable insertion and removal in a sanitary and easy fashion.

The materials that the product can be made from are varied but in one embodiment it is made of a white, antimicrobial, absorbent, 12 oz 50/50 cotton/polypropylene blend. The sizes of the product are also varied, but can be for example 6.5" long and 1 inch wide, or and 8" long by 1.25" wide.

There can also be a 0.125" (⅛") seal line on edge for material to keep shape and to keep from fraying.

What is claimed is:

1. A method for maintaining an intergluteal cleft in a dry condition, the method comprising the steps of:
   providing a personal hygiene product, the personal hygiene product having an absorbent substrate with a proximal end and a distal end;
   inserting the personal hygiene product into the intergluteal cleft of a user;
   absorbing sweat with the personal hygiene product; and
   removing the absorbent substrate from the intergluteal cleft of the user using a first handle and a second handle of the personal hygiene product, in which a tether extends through the absorbent substrate having a first end and a second end, the first end extending past the absorbent substrate proximal end, the second end extending past the absorbent substrate distal end, and the absorbent substrate is a flat sheet that is rolled over onto itself around the tether, and the first end forming the first handle and the second end forming the second handle.

2. The method of maintaining the intergluteal cleft in a dry condition of claim 1, further including manufacturing the absorbent substrate from cotton.

3. The method of maintaining the intergluteal cleft in a dry condition of claim 1, further including manufacturing the absorbent substrate from paper.

4. The method of maintaining the intergluteal cleft in a dry condition of claim 1, further including providing the absorbent substrate with a cross-section shape selected from the group of shapes consisting of flat, round, oval, circular and triangular.

5. The method of maintaining the intergluteal cleft in a dry condition of claim 1, further including providing a layer of powder over the absorbent substrate.

6. The method of maintaining the intergluteal cleft in a dry condition of claim 1, further including providing the absorbent substrate with a scent.

* * * * *